(12) United States Patent
Takagi et al.

(10) Patent No.: US 8,569,553 B2
(45) Date of Patent: Oct. 29, 2013

(54) PROCESS FOR PRODUCING 2,3,3,3-TETRAFLUOROPROPENE

(75) Inventors: Hirokazu Takagi, Tokyo (JP); Hidekazu Okamoto, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/167,464

(22) Filed: Jun. 23, 2011

(65) Prior Publication Data

US 2011/0319679 A1 Dec. 29, 2011

Related U.S. Application Data

(60) Provisional application No. 61/365,575, filed on Jul. 19, 2010.

(30) Foreign Application Priority Data

Jun. 23, 2010 (JP) .................................. 2010-142668

(51) Int. Cl.
*C07C 19/08* (2006.01)
(52) U.S. Cl.
USPC .......................................................... 570/176
(58) Field of Classification Search
None
See application file for complete search history.

(56) References Cited

U.S. PATENT DOCUMENTS

| 5,171,901 A * | 12/1992 | Gassen et al. .................. 570/168 |
| 5,315,047 A * | 5/1994 | Lui et al. ......................... 570/168 |
| 2010/0022808 A1 | 1/2010 | Rao et al. |

FOREIGN PATENT DOCUMENTS

| EP | 396974 A1 * | 11/1990 |
| JP | 2-286635 | 11/1990 |
| JP | 3-163033 | 7/1991 |
| JP | 7-138194 | 5/1995 |
| JP | 2005-225767 | 8/2005 |
| JP | 2010-510221 | 4/2010 |
| WO | WO 2008/060614 | 5/2008 |

OTHER PUBLICATIONS

U.S. Appl. No. 13/167,455, filed Jun. 23, 2011, Okamoto.
U.S. Appl. No. 13/167,285, filed Jun. 23, 2011, Seki, et al.
U.S. Appl. No. 13/167,235, filed Jun. 23, 2011, Kawaguchi, et al.
U.S. Appl. No. 13/167,509, filed Jun. 23, 2011, Kawaguchi, et al.
U.S. Appl. No. 13/167,145, filed Jun. 23, 2011, Takagi, et al.
U.S. Appl. No. 13/167,254, filed Jun. 23, 2011, Kawaguchi, et al.
International Search Report issued Sep. 27, 2011, in PCT/JP2011/064427 (with English Translation of Category of Cited Documents).

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The object is to provide a process whereby it is possible to produce 2,3,3,3-tetrafluoropropene at a high conversion ratio constantly for a long period of time.

A process for producing 2,3,3,3-tetrafluoropropene, which comprises reacting a raw material compound of at least one of 1,1-dichloro-2,3,3,3-tetrafluoropropene and 1-chloro-2,3,3,3-tetrafluoropropene, and hydrogen, in the presence of a catalyst, wherein the catalyst is a noble metal catalyst supported on a metal oxide having a Hammett acidity function value ($H_0$) of at least −5.6.

18 Claims, 1 Drawing Sheet

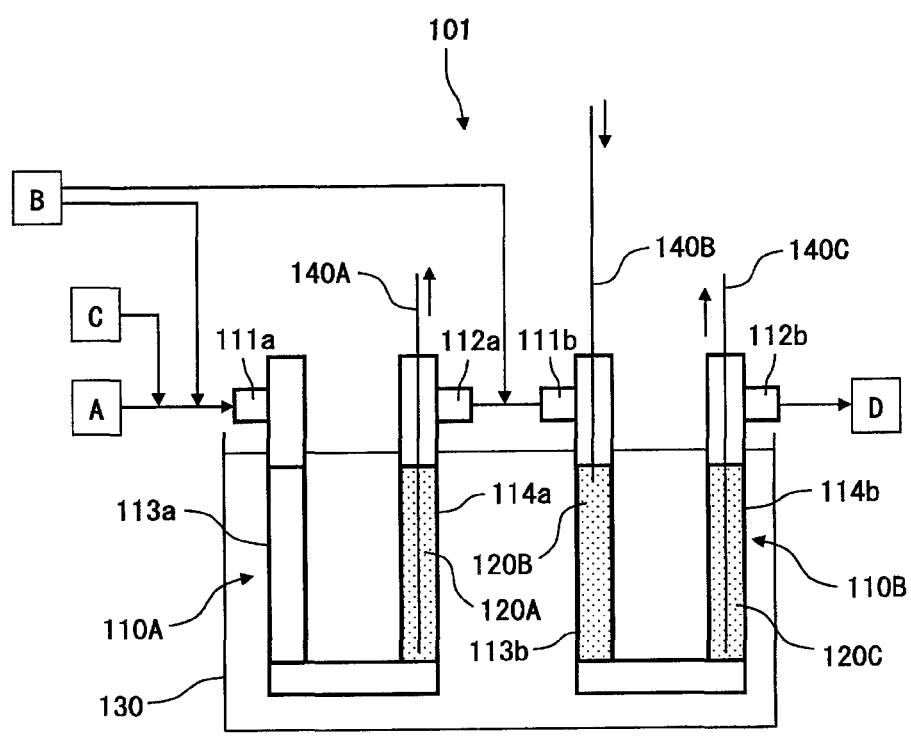

PROCESS FOR PRODUCING 2,3,3,3-TETRAFLUOROPROPENE

TECHNICAL FIELD

The present invention relates to a process for producing 2,3,3,3-tetrafluoropropene.

BACKGROUND ART 2,3,3,3-Tetrafluoropropene ($CF_3CF=CH_2$, HFO-1234yf) contains no chlorine and thus is useful as an alternative compound for chlorofluorocarbons to be used for e.g. refrigerants.

As a process for producing HFO-1234yf, a process may, for example, be mentioned wherein 1,1-dichloro-2,2,3,3,3-pentafluoropropane ($CF_3CF_2CHCl_2$, HCFC-225ca) is subjected to a dehydrofluorination reaction to obtain 1,1-dichloro-2,3,3,3-tetrafluoropropene ($CF_3CF=CCl_2$, CFO-1214ya), and then, CFO-1214ya is reacted with hydrogen and reduced to obtain HFO-1234yf.

As a method of reducing CFO-1214ya to obtain HFO-1234yf, the following method (i) may, for example, be mentioned.

(i) A method for obtaining HFO-12-34yf by reacting CFO-1214ya and hydrogen in the presence of a catalyst having palladium supported on alumina (Patent Document 1).

However, the catalyst used in the method (i) has a drawback such that while the durability is high, side reactions are substantial to form by-products which can hardly be separated by distillation, and the conversion ratio to HFO-1234yf is low.

On the other hand, as a method for carrying out a similar reduction reaction, the following method (ii) has been proposed.

(ii) a method of reacting $RfCF=CX_2$ (wherein Rf is a $C_{1-10}$ fluoroalkyl group, and X is chlorine, bromine or iodine) with hydrogen in the presence of a catalyst having palladium supported on active carbon, to obtain $RfCF=CH_2$ (Patent Document 2).

However, the catalyst used in the method (ii) has low durability in many cases, whereby it is required to change the catalyst frequently.

PRIOR ART DOCUMENTS

Patent Documents

Patent Document 1: WO2008/060614
Patent Document 2: JP-A-2-286635

DISCLOSURE OF INVENTION

Technical Problem

It is an object of the present invention to provide a process for producing 2,3,3,3-tetrafluoropropene at a high conversion ratio constantly for a long period of time.

Solution to Problem

In order to solve the above problem, the present invention has adopted the following construction.

[1] A process for producing 2,3,3,3-tetrafluoropropene, which comprises reacting a raw material compound of at least one of 1,1-dichloro-2,3,3,3-tetrafluoropropene and 1-chloro-2,3,3,3-tetrafluoropropene, and hydrogen, in the presence of a catalyst, wherein the catalyst is a noble metal catalyst supported on a metal oxide having a Hammett acidity function value ($H_0$) of at least −5.6.

[2] The process for producing 2,3,3,3-tetrafluoropropene according to the above [1], wherein the noble metal is palladium.

[3] The process for producing 2,3,3,3-tetrafluoropropene according to the above [1] or [2], wherein the metal oxide is silicon dioxide, titanium dioxide or zirconium dioxide.

[4] The process for producing 2,3,3,3-tetrafluoropropene according to any one of the above [1] to [3], wherein the metal oxide is silicon dioxide.

[5] The process for producing 2,3,3,3-tetrafluoropropene according to any one of the above [1] to [4], wherein the noble metal catalyst-supporting metal oxide has a specific surface area of from 10 to 1,000 $m^2/g$.

[6] The process for producing 2,3,3,3-tetrafluoropropene according to any one of the above [1] to [5], wherein to a catalyst layer packed with the catalyst-supporting metal oxide, the raw material compound and the hydrogen are introduced and reacted in a gas phase.

[7] The process for producing 2,3,3,3-tetrafluoropropene according to the above [6], wherein the raw material compound and the hydrogen are introduced to a gas inlet portion of the catalyst layer, and hydrogen is introduced from at least one position between the gas inlet portion and a gas outlet portion of the catalyst layer.

[8] The process for producing 2,3,3,3-tetrafluoropropene according to the above [6] or [7], wherein the ratio of the hydrogen to the raw material compound to be introduced to the catalyst layer is at most 0.7 as represented by the ratio of the number of moles of the hydrogen to the number of moles of chlorine atoms in the raw material compound ($H_2/Cl$).

[9] The process for producing 2,3,3,3-tetrafluoropropene according to any one of the above [6] to [8], wherein the linear velocity u of the raw material compound gas represented by the following formula (I) in the catalyst layer is from 1 to 30 cm/sec:

$$u=(W/100) \times V/S \quad (I)$$

(in the formula (I), W is the concentration (mol %) of the raw material compound gas in the entire gas flowing through the catalyst layer, V is the flow rate ($cm^3/sec$) of the entire gas flowing through the catalyst layer, and S is the cross-sectional area ($cm^2$) of the catalyst layer to the flow direction of the gas.)

[10] The process for producing 2,3,3,3-tetrafluoropropene according to any one of the above [1] to [9], wherein the raw material compound is 1,1-dichloro-2,3,3,3-tetrafluoropropene, or a mixture of 1,1-dichloro-2,3,3,3-tetrafluoropropene and 1-chloro-2,3,3,3-tetrafluoropropene wherein-based on the total number of moles of the two, the proportion of 1,1-dichloro-2,3,3,3-tetrafluoropropene is at least 50 mol %.

Advantageous Effects of Invention

According to the process of the present invention, it is possible to produce 2,3,3,3-tetrafluoropropene at a high conversion ratio constantly for a long period of time.

BRIEF DESCRIPTION OF DRAWING

FIG. 1 is a schematic view illustrating a production apparatus used in Examples.

DESCRIPTION OF EMBODIMENT

The process for producing 2,3,3,3-tetrafluoropropene ($CF_3CF=CH_2$, HFO-1234yf) of the present invention is a process wherein a raw material compound of at least one of 1,1-dichloro-2,3,3,3-tetrafluoropropene (CF$_3$CF=CCl$_2$, CFO-1214ya) and 1-chloro-2,3,3,3-tetrafluoropropene (CF$_3$CF=CHCl, HCFO-1224yd), and hydrogen, are reacted in the presence of a catalyst.

CFO-1214ya and HCFO-1224yd will form HFO-1234yf by the reactions represented by the following formulae (1) and (2), respectively.

$$CF_3CF=CCl_2+2H_2 \rightarrow CF_3CF=CH_2+2HCl \quad (1)$$

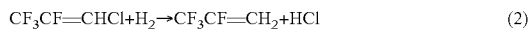
$$CF_3CF=CHCl+H_2 \rightarrow CF_3CF=CH_2+HCl \quad (2)$$

The process of the present invention may be the following process (α) or process (β) depending upon the reaction form.

(α) A process of reacting the raw material compound and hydrogen in a gas phase in the presence of a catalyst.

(β) A process of reacting the raw material compound and hydrogen in a liquid phase in the presence of a catalyst.

(Process (α))

The process (α) may, for example, be a process wherein a catalyst layer packed with a catalyst-supporting carrier is formed, and to such a catalyst layer, a gas (hereinafter referred to also as the raw material mixed gas) comprising the raw material compound gas and hydrogen gas is introduced and reacted.

As the catalyst, a noble metal catalyst supported on a metal oxide having a Hammett acidity function value (H$_0$) of at least −5.6, is used. By using such a metal oxide as a carrier, it is possible to obtain a catalyst having high durability, and the conversion ratio from the raw material compound to HFO-1234yf can be made high. The acidity function value (H$_0$) of the metal oxide is preferably at least −0.30, since it is thereby easy to attain both the conversion ratio and durability. Further, the acidity function value (H$_0$) is preferably at most +3.3, since it is thereby easy to suppress side reactions such as dehydrochlorination, dehydrofluorination, etc.

The Hammett acidity function value (H$_0$) can be measured by the following Hammett's indicator adsorption method. A metal oxide is maintained in saturated water vapor at 25° C. for two days, whereupon benzene is added to form a benzene solution containing the metal oxide, to which Hammett's indicator is dropwise added, whereby coloration of the acid color on the metal oxide is confirmed. If the acidity function value (H$_0$) of the metal oxide is smaller than the pKa of the Hammett's indicator, coloration of the acid color is observed. Such confirmation of the coloration of the acid color may be carried out by visual observation or by a spectroscopic means.

In the present invention, a metal oxide having an acidity function value (H$_0$) of at least −5.6 is such a metal oxide that no coloration of the acid color is observed when a Hammett's indicator having a pKa of −5.6 is dropwise added in the above indicator adsorption method.

The Hammett's indicators include, for example, benzal acetophenone (pKa: −5.6), dicinnamal acetone (pKa: −3.0), 4-benzene azodiphenylamine (pKa: +1.5), p-dimethylaminoazobenzene (pKa: +3.3), phenylazonaphthylamine (pKa: +4.0), methyl red (pKa: +4.8), etc.

The metal oxide having an acidity function value (H$_0$) of at least −5.6 may, for example, be silicon dioxide (+1.5≥H$_0$>−5.6), titanium dioxide (+1.5≥H$_0$>−5.6), or zirconium dioxide (H$_0$>+1.5). Such metal oxides may be used alone, or two or more of them may be used in combination.

The metal oxide is preferably silicon dioxide, titanium dioxide or zirconium dioxide, particularly preferably silicon dioxide, whereby it is easy to attain both the conversion ratio and durability. Further, in a case where silicon dioxide is used as a carrier, it is preferred to use silica gel, amorphous silica or the like.

The noble metal as the catalyst may, for example, be palladium, rhodium, platinum, iridium, ruthenium, osmium or gold. The noble metal to be supported on the metal oxide may be one type, or two or more types. When two or more noble metals are used as the catalyst, the catalyst may be a mixture or alloy of noble metals. The alloy catalyst may, for example, be a palladium/platinum alloy catalyst or a palladium/rhodium alloy catalyst.

As the noble metal to be supported on the metal oxide, from the viewpoint of the activity, palladium, rhodium or platinum is preferred, and palladium or a palladium alloy is particularly preferred.

The supported amount of the noble metal is preferably from 0.01 to 10 mass %, more preferably from 0.1 to 10 mass %, particularly preferably from 0.5 to 1 mass %, based on the metal oxide. When the supported amount of the noble metal is at least the lower limit value, the conversion of the raw material compound and hydrogen will be improved. When the supported amount of the noble metal is at most the upper limit value, the costs for the catalyst can be reduced, and such a catalyst may be easily available.

As the catalyst to be used for the process of the present invention, palladium is particularly preferred.

Further, the catalyst-supporting metal oxide to be used in the process of the present invention may have a metal other than a noble metal supported in addition to the noble metal, for example, with a view to suppressing by-products or improving the catalyst durability. As the metal other than a noble metal, iron, cobalt or nickel may, for example, be mentioned. Such metals other than a noble metal may be used alone or in combination as a mixture of two or more of them.

In a case where a metal other than a noble metal is to be supported, the proportion of such a metal is preferably from 0.01 to 50 parts by mass per 100 parts by mass of the noble metal.

The specific surface area of the catalyst is preferably from 10 to 1,000 m$^2$/g, more preferably from 100 to 500 m$^2$/g. When the specific surface area of the catalyst is at least the lower limit value, the conversion of the raw material compound and hydrogen will be improved. When the specific surface area of the catalyst is at most the upper limit value, formation of by-products can easily be suppressed.

The specific surface area of the catalyst is measured by a gas adsorption method, e.g. a method in accordance with BET method.

The catalyst layer in the present invention is formed by packing the above-described noble metal catalyst-supporting metal oxide in a reactor. The packed density of the catalyst-supporting metal oxide in the catalyst layer is preferably from 0.1 to 3 g/cm$^3$, more preferably from 0.25 to 1 g/cm$^3$. When the packed density of the catalyst-supporting metal oxide is at least the lower limit value, the packed amount of the catalyst-supporting metal oxide per unit volume is large, whereby the amount of gas to be reacted can be increased, and the productivity will be improved. When the packed density of the catalyst-supporting metal oxide is at most the upper limit value, the temperature rise of the catalyst layer can easily be controlled, and it becomes easy to maintain the reaction temperature to be at most 130° C.

In the reactor, there may be one or more portions packed with the catalyst-supporting metal oxide.

The temperature of the catalyst layer is adjusted to be higher than the dew point of the gas comprising the raw material compound gas and hydrogen gas, since the reaction is a gas phase reaction. It is preferably at least 50° C., more preferably at least 60° C., since the boiling point of CFO-1214ya is 46° C. and the boiling point of HCFO-1224yd is assumed to be from 4 to 10° C., and in view of the reactivity.

The temperature of the catalyst layer gradually decreases along with the progress of deterioration of the catalyst, thus leading to a problem that the conversion decreases. Therefore, it is preferred to carry out an operation to maintain the temperature of the catalyst layer at a sufficient temperature level so that the high conversion can be maintained. For example, in a case where the catalyst layer is heated from outside by e.g. a heating medium to maintain its temperature, it is possible to gradually increase the temperature of the heating medium thereby to increase the temperature of the catalyst layer.

Here, the temperature of the catalyst layer is the temperature of the catalyst layer which is maintained by heating from outside. Usually, the raw material mixed gas is reacted at a part of the region of the catalyst layer, and a reaction zone (the region where the raw material mixed gas is reacted) becomes a higher temperature than other regions of the catalyst layer, by generation of heat of reaction. The catalytic activity in this reaction zone will decrease as time passes, and usually, the reaction zone gradually moves from the inlet of the raw material mixed gas to the downstream side in the gas flow direction. Further, on the downstream side of the reaction zone, formed gas having a high temperature, formed in the reaction zone, flows and usually the temperature becomes higher than the temperature of the catalyst layer, and the temperature gradually decreases as the distance increases from the reaction zone. In the present invention, the temperature of the catalyst layer is the temperature on the upstream side of the reaction zone i.e. the temperature of the catalyst layer, of which the temperature is maintained by heating from outside by e.g. a heating medium.

Further, in the process of the present invention, the maximum temperature of the catalyst layer is maintained to be preferably at most 130° C., more preferably at most 100° C. during the reaction with a view to suppressing formation of by-products. That is, in the process of the present invention, it is preferred to suppress an excessive temperature rise of the catalyst layer due to the heat of reaction, so that the maximum temperature of the catalyst layer will be at most the above upper limit value. As mentioned above, the temperature in the region where the raw material mixed gas is reacted and in a region in the vicinity on the downstream side thereof becomes higher than the temperature of the catalyst layer in other regions, due to the heat of reaction. The maximum temperature in the catalyst layer during the reaction is the maximum temperature in a region of the catalyst layer where the temperature is higher than other regions, due to generation of such heat of reaction.

As a method for measuring the maximum temperature of the catalyst layer during the reaction, the following measuring method employing an insertion-type thermometer may, for example, be mentioned.

In the reaction of the raw material compound and the hydrogen in the catalyst layer, firstly, the catalyst at the gas inlet portion contributes to the reaction, and as the catalyst at the gas inlet portion deteriorates, the catalyst on the downstream side thereof will contribute to the reaction, and in such a manner, the reaction zone in the catalyst layer gradually moves towards to the gas outlet side. That is, the portion showing the maximum temperature of the catalyst layer moves along with the movement of the reaction zone of the raw material compound gas and the hydrogen gas. Accordingly, by preliminarily positioning the measuring portion of the insertion-type thermometer at the gas inlet portion of the catalyst layer and moving the measuring portion along with the progress of the reaction, the maximum temperature of the catalyst layer can be measured.

As a method to maintain the maximum temperature of the catalyst layer during the reaction to be at most the above upper limit value, a method (method ($\alpha$1)) of introducing the hydrogen dividedly to the catalyst layer is preferred from such a viewpoint that the productivity can easily be maintained to be high while controlling the maximum temperature of the catalyst layer to be low. If the hydrogen is introduced dividedly to plural portions of the catalyst layer, it is possible to disperse the reaction zones in the catalyst layer without changing the amount of the raw material compound to be introduced, whereby generation of the heat of reaction is not localized at one portion. Therefore, it is possible to easily suppress local excessive heat generation in the catalyst layer without lowering the productivity.

The divided introduction of hydrogen means that at the same time as introducing the raw material compound and hydrogen to the gas inlet portion of the catalyst layer, hydrogen is introduced from at least one portion between the gas inlet portion and the gas outlet portion of the catalyst layer. That is, it means that hydrogen is introduced from at least one portion in the catalyst layer in addition to the inlet portion for introducing the raw material mixed gas, i.e. from a total of at least two positions.

Specifically, the raw material mixed gas to be introduced to the gas inlet portion (the gas inlet portion on the most upstream side in the gas flow direction) in the catalyst layer, is a mixed gas of the total amount of the raw material compound and a part of hydrogen to be introduced to the catalyst layer. The rest of hydrogen is introduced to the catalyst layer on the downstream side in the gas flow direction, and the hydrogen is mixed to a gas (usually a formed gas after a part of the raw material compound is reacted with hydrogen) flowing in the catalyst layer at the introduction position, and an unreacted raw material compound is reacted with hydrogen in the catalyst layer on the downstream side from the introduction position of the hydrogen, whereupon the formed gas is discharged from the outlet of the catalyst layer (the gas discharge portion on the most downstream side in the gas flow direction). It is preferred that at least a part of hydrogen in the raw material mixed gas is reacted with the raw material compound between the inlet portion of the raw material mixed gas and the next hydrogen introduction portion. Further, the hydrogen-introduction portion on the most downstream side in the gas flow direction is preferably provided at a position where the introduced hydrogen and the raw material compound can sufficiently be reacted in the catalyst layer between the hydrogen-introduction portion and the gas outlet portion.

Introduction of the hydrogen in the method ($\alpha$1) may be divided into two portions or divided into three or more portions. It is preferred to divide the introduction into two portions, whereby the process can be simplified.

The divided proportions of the hydrogen to be introduced dividedly to at least two portions in the catalyst layer are preferably such that the respective gas amounts divided are equal amounts, whereby it is easy to maintain the maximum temperature of the catalyst layer to be low.

In a case where there are two or more portions packed with the catalyst-supporting metal oxide in the reactor, the divided introduction of the hydrogen may, for example, be carried out by a method wherein a part of the hydrogen is introduced together with the raw material compound to the first stage packed portion, and the rest is introduced to the packed portions of the second or subsequent stages.

Further, as a method for controlling the maximum temperature of the catalyst layer other than the method (α1), a method (method (α2)) of letting an inert gas flow in the catalyst layer together with the raw material compound and the hydrogen, may be mentioned. By adjusting the concentration of the raw material compound and the hydrogen flowing in the catalyst layer by letting the inert gas flow, it is possible to suppress an excessive temperature rise of the catalyst layer by a heat of reaction. Further, it is possible to use a diluting gas other than an inert gas instead of the inert gas or together with the inert gas.

As such an inert gas, nitrogen gas, rare gases or chlorofluorocarbons inert to the hydrogenation reaction may, for example, be mentioned. As the diluting gas other than an inert gas, hydrogen chloride may, for example, be mentioned.

The amount of the inert gas to be introduced to the catalyst layer is preferably at least 0.1 mol, more preferably at least 0.5 mol, per 1 mol of the raw material compound, from such a viewpoint that it is thereby easy to maintain the maximum temperature of the catalyst layer to be low, to reduce formation of by-products and to suppress deterioration of the catalyst. Further, the amount of the inert gas to be introduced is preferably at most 10 mol, more preferably at most 4 mol, per 1 mol of the raw material compound, from the viewpoint of the recovery rate of the inert gas.

Further, as a method for controlling the maximum temperature of the catalyst layer other than the method (α1) and the method (α2), a method (method (α3)) may be mentioned wherein the temperature of heating medium to heat the reactor is made lower, while the lower limit is the dew point of the raw material mixed gas. By keeping the temperature of the heating medium to be low, a more swift heat removal of the heat of reaction becomes possible, and an excessive temperature rise of the catalyst layer can be suppressed.

In the method (α3), the temperature of the catalyst layer is preferably adjusted to be higher than the dew point and lower than 50° C., since the temperature being lower is advantageous in order to suppress formation of by-products which are hardly separable from HFO-1234yf. More preferably, it is higher than the dew point and at most 30° C.

For the control of the maximum temperature of the catalyst layer, the method (α1), the method (α2) or the method (α3) may preferably be used alone, or two or three of them may preferably be used in combination.

The reaction pressure is preferably atmospheric pressure from the viewpoint of the operation efficiency, but it is not particularly limited and may be reduced pressure or elevated pressure.

The contact time of the raw material compound gas to the catalyst is preferably from 4 to 60 seconds, more preferably from 8 to 40 seconds. Such a contact time is a contact time of the raw material compound gas, which is calculated from the volume of the catalyst layer and the amount of the gas to be introduced to the reactor.

The ratio of the hydrogen to the raw material compound to be introduced to the catalyst layer is such that the ratio of the number of moles of the hydrogen to the number of moles of chlorine atoms in the raw material compound ($H_2/Cl$) is made to be preferably at most 0.7, more preferably at most 0.6, further preferably at most 0.5, from such a viewpoint that formation of by-products can thereby be easily suppressed. Further, the ratio ($H_2/Cl$) is preferably at least 0.1, more preferably at least 0.2, from the viewpoint of the yield of HFO-1234yf.

Also In a case where the hydrogen is dividedly introduced, with respect to the ratio of the total amount of hydrogen to be introduced to the catalyst layer to the raw material compound to be introduced to the catalyst layer, the above-mentioned ratio in the number of moles ($H_2/Cl$) is likewise adjusted to be preferably at most 0.7, more preferably at most 0.6, further preferably at most 0.5. Further, the ratio ($H_2/Cl$) is preferably at least 0.1, more preferably at least 0.2.

In the process of (α), the linear velocity u of the raw material compound gas represented by the following formula (I) in the catalyst layer is preferably from 0.1 to 100 cm/sec., more preferably from 1 to 30 cm/sec. Such a linear velocity u is a linear velocity of the raw material compound gas which is calculated from the volume of the catalyst layer and the amount of the gas to be introduced to the reactor. When the linear velocity u of the raw material compound gas is at least the lower limit value, the productivity will be improved. Especially when the gas linear velocity is at least 1 cm/sec., the gas is likely to flow uniformly in the catalyst layer. When the linear velocity u of the raw material compound gas is at most the upper limit, the conversion of the raw material compound and the hydrogen will be improved. Especially when the gas linear velocity is at most 30 cm/sec., the temperature control in the vicinity of the reaction point due to heat generation will be easy.

$$u=(W/100) \times V/S \tag{I}$$

In the formula (I), W is the concentration (mol %) of the raw material compound gas in the entire gas flowing through the catalyst layer, V is the flow rate ($cm^3$/sec) of the entire gas flowing through the catalyst layer, and S is the cross-sectional area ($cm^2$) of the catalyst layer to the flow direction of the gas.

As a reactor to be used for the process (α), a known reactor capable of forming a catalyst layer having a catalyst-supporting carrier packed, may be mentioned.

As the material for the reactor, glass, iron, nickel or an alloy containing such a metal as the main component may, for example, be mentioned.

The formed gas after the reaction contains, in addition to the desired product HFO-1234yf, an unreacted raw material, HCFO-1224yd formed as a reaction intermediate and hydrogen chloride.

Hydrogen chloride contained in the formed gas can be removed by blowing the formed gas into an alkali aqueous solution for its neutralization. The alkali to be used for such an alkali aqueous solution may, for example, be sodium hydroxide or potassium hydroxide.

As a method for recovering HFO-1234yf, an unreacted raw material and a reaction intermediate compound from the formed gas, a known method such as distillation may, for example, be employed.

The unreacted raw material and reaction intermediate recovered from the formed gas after the reaction can be re-used. The recovered HCFO-1224yd may be reacted as a raw material compound together with CFO-1214ya, with hydrogen, or separately from CFO-1214ya, HCFO-1224yd may be reacted alone with hydrogen.

In a case where a mixture of CFO-1214ya and HCFO-1224yd is used as the raw material compound gas, it is common to use a mixture having a small proportion of HCFO-1224yd, since HCFO-1224yd is an intermediate at the time of obtaining HFO-1234yf from the above CFO-1214ya. Accordingly, the proportion of HCFO-1224yd to the total amount of CFO-1214ya and HCFO-1224yd is preferably at most 50 mol %, more preferably at most 25 mol %.

(Process (β))

In the process (β), the raw material compound and hydrogen are reacted in a liquid phase in the presence of a catalyst.

The catalyst and the catalyst-supporting carrier are the same as the ones described for the process (α).

In the process (β), a medium may be used or may not be used. However, it is preferred to use a medium. As such a medium, water or an organic solvent such as an alcohol may, for example, be mentioned.

In a case where a medium is used, the amount of the medium is preferably from 10 to 100 parts by mass, per 100 parts by mass of the raw material compound.

A method for supplying hydrogen may, for example, be a method of blowing hydrogen gas to a liquid containing a catalyst-supporting carrier, the raw material compound and a medium which is used as the case requires, or a method of adding a medium having hydrogen preliminarily dissolved under pressure to a liquid containing the catalyst-supporting carrier and the raw material compound.

The reaction of the raw material compound and hydrogen in the process (β) may be a batch system or a continuous system.

The reaction temperature is preferably from 0 to 150° C., more preferably from 20 to 100° C. When the reaction temperature is at least the lower limit-value, the conversion of the raw material compound and hydrogen will be improved. When the reaction temperature is at most the upper limit value, it is easy to suppress formation of by-products.

The reaction pressure is preferably from 0.01 to 5 MPaG, more preferably from 0.1 to 1 MPaG.

The reaction time is preferably from 5 to 50 hours in the case of a batch system, and it is preferably from 1 to 60 seconds in the case of a continuous system.

With respect to the supply amount of hydrogen in the process (β), the ratio of the number of moles of hydrogen to the number of moles of chlorine atoms in the raw material compound ($H_2$/Cl) is made to be preferably at most 0.7, more preferably at most 0.5, from such a viewpoint that formation of by-products can thereby be easily suppressed. Further, the ratio ($H_2$/Cl) is preferably at least 0.1, more preferably at least 0.2, from the viewpoint of the yield of HFO-1234yf. Here, the supply amount of hydrogen is meant for the amount of hydrogen dissolved in the reaction solution.

The reaction solution after the reaction contains, in addition to the desired product HFO-1234yf, an unreacted raw material, HCFO-1224yd formed as a reaction intermediate and hydrogen chloride. The hydrogen chloride contained in the reaction solution can be removed by adding an alkali to the reaction solution for its neutralization. Such an alkali may, for example, be sodium hydroxide or potassium hydroxide. The alkali may preliminarily be added to a reaction solution to be used for the reaction.

As a method for recovering HFO-1234yf, an unreacted raw material and reaction intermediate compound from the reaction solution, a known method such as distillation may, for example, be employed.

The unreacted raw material and the reaction intermediate recovered from the reaction solution can be re-used. The recovered HCFO-1224yd may be reacted as a raw material-compound together with CFO-1214ya with hydrogen, or separately from CFO-1214ya, HCFO-1224yd may be reacted alone with hydrogen.

As a reactor to be used for the process (β), a known reactor capable of carrying out the liquid phase reaction by contacting the reaction raw material in the presence of the catalyst-supporting carrier. As the material for the reactor, glass, iron, nickel or an alloy containing such a metal as the main component may, for example, be mentioned.

(Raw Material Compound)

The raw material compound is composed of at least one of CFO-1214ya and HCFO-1224yd.

CFO-1214ya can be produced by a known method. For example, a method may be mentioned wherein 1,1-dichloro-2,2,3,3,3-pentafluoropropane ($CHCl_2CF_2CF_3$, HCFC-225ca) is subjected to a dehydrofluorination reaction by contacting it with an alkali aqueous solution in the presence of a phase-transfer catalyst. For such a reaction, dichloropentafluoropropane (HCFC-225) including HCFC-225ca may be used, and only HCFC-225ca in HCFC-225 may selectively be dehydrofluorinated by the above phase-transfer catalyst. After the reaction, CFO-1214ya can be separated and recovered by a known method such as distillation.

The above HCFC-225 including HCFC-225ca can be produced by reacting tetrafluoroethylene and dichlorofluoromethane in the presence of a catalyst such as aluminium chloride. The mixture of isomers obtainable by such a reaction contains HCFC-225ca and 1,3-dichloro-1,2,2,3,3-pentafluoropropane ($CHClFCF_2CClF_2$, HCFC-225cb) as the main components, and further contains a small amount of 2,2-dichloro-1,1,3,3,3-pentafluoropropane ($CHF_2CCl_2CF_3$, HCFC-225aa), 2,3-dichloro-1,1,2,3,3-pentafluoropropane ($CHF_2CClFCClF_2$, HCFC-225bb), etc.

As such HCFC-225 including HCFC-225ca, a commercial product may be employed. As such a commercial product, ASAHIKLIN AK225 (tradename, manufactured by Asahi Glass Company, Limited, mixture of 48 mol % of HCFC-225ca and 52 mol % of HCFC-225cb) may, for example, be mentioned.

As the above phase-transfer catalyst, tetrabutylammonium bromide (TBAB) is preferred.

HCFO-1224yd is formed as an intermediate at the time of obtaining HFO-1234yf by reacting CFO-1214ya with hydrogen.

As described in the foregoing, in the process of the present invention, as the catalyst carrier, a metal oxide having a high durability as compared with active carbon, is used. Further, the Hammett acidity function value ($H_0$) of the metal oxide to be used is at least −5.6, whereby the conversion ratio from the raw material compound to HFO-1234yf is high by the use of the noble metal catalyst supported on such a carrier. Therefore, according to the process of the present invention, it is possible to produce HFO-1234yf at a high conversion ratio constantly for a long period of time.

EXAMPLES

Now, the present invention will be described in further detail with reference to Examples and Comparative Examples. However, it should be understood that the present invention is by no means restricted by the following description. Example 2 is a working Example of the present invention, and Example 3 is a Comparative Example.

[Measurement of Conversion Ratio]

Formed gas obtained in each Example was analyzed by gas chromatography (GC), and conversion ratio X (unit: %) from CFO-1214ya to HFO-1234yf was calculated by the following formula (II). The measurement of the conversion ratio X was carried out at the initial stage of the reaction and upon expiration of time as shown in Table 1.

$$X=[Y/(Z/2)]\times 100 \qquad (II)$$

(in the formula, Y is the number of moles of formed HFO-1234yf, and Z is the number of moles of CFO-1214ya introduced to the catalyst layer.)

Example 1

Production of CFO-1214ya

CFO-1214ya was produced by the following method by using, as a reaction raw material, ASAHIKLIN AK225

(tradename, manufactured by Asahi Glass Company, Limited, HCFC-225 composed of HCFC-225ca (48 mol %) and HCFC-225cb (52 mol %).

Into a glass reactor having an internal capacity of 1 L and provided with a Dimroth condenser cooled to 0° C., 3 g of tetrabutylammonium bromide (TBAB) as a phase-transfer catalyst, 83 g (1.485 mol) of potassium hydroxide, 180 g of water, and 609 g (3.0 mol) of ASAHIKLIN AK225 were charged and then gradually heated with stirring, and a reaction was carried out at 45° C. for one hour. Thereafter, the reaction crude liquid phase-separated into two phases of an organic phase and an aqueous phase, was subjected to liquid separation. The organic phase was charged into a distillation column having an oven capacity of 1 L and an ability of theoretical number of plates of 10 plates, and distillation was carried out. As a result of the distillation, 262 g (1.43 mol) of CFO-1214ya (boiling point: 46° C.) having a purity of 99.5%, was obtained.

Example 2

For the production of HFO-1234yf, a reaction apparatus 101 shown in FIG. 1 was used.

As shown in FIG. 1, the reaction apparatus 101 is provided with two reaction tubes 110A and 110B and an oil bath 130 for immersion of such reaction tubes 110A and 110B. The reaction tube 110A has catalyst-packing portions 113a and 114a at two positions on the inlet 111a side and the outlet 112a side. Likewise, the reaction tube 110B has catalyst-packing portions 113b and 114b at two positions on the inlet 111b side and the outlet 112b side. The outlet 112a of the reaction tube 110A is connected by piping to the inlet 111b of the reaction tube 110B.

As the reaction tubes 110A and 110B, reaction tubes made of Inconel (registered trademark) 600 and having an inner diameter of 2.54 cm and a length of 100 cm, were used. Further, palladium-supporting silica gel (specific surface area: 100 m$^2$/g) having 0.5 mass % of palladium supported on silica gel (+1.5>H$_0$>−5.6), was used. Such a palladium-supporting silica gel was packed in the catalyst-packing portion 114a of the reaction tube 110A to form a catalyst layer 120A having a height of 40 cm. Likewise, the above palladium-supporting silica gel was packed in the catalyst-packing portions 113b and 114b of the reaction tube 110B to form a catalyst layer 120B and a catalyst layer 120C each having a height of 40 cm. The packed density of the palladium-supporting carrier in catalyst layers 120A to 120C was adjusted to be 0.47 g/cm$^3$.

Then, the reaction tube 110A and the reaction tube 110B were immersed in the oil bath 130 so that all of the catalyst layers 120A to 120C were immersed, and the catalyst layers 120A to 120C were heated to 80° C.

Then, a raw material compound gas (A) composed of CFO-1214ya, hydrogen gas (B) and nitrogen gas (C) were permitted to flow through reaction tubes 110A and 1110B in a molar ratio of the total introduced amounts being hydrogen/CFO-1214ya/nitrogen=1/1/2 to obtain formed gas (D). That is, the ratio of the total number of moles of the hydrogen gas (B) to be introduced to the catalyst layer to the number of moles of chlorine atoms in the raw material compound gas (A) (H$_2$/Cl) was made to be 0.5. Further, the contact time of the raw material compound gas (A) to the catalyst layers 120A to 120C was adjusted to be 40 seconds, and the linear velocity u of the raw material compound gas (A) was adjusted to be 7 cm/sec.

Further, with respect to the hydrogen gas (B), 50% of the total introduced amount was introduced from the inlet 111a of the reaction tube 110A together with the raw material compound gas (A), and the rest of 50% was introduced to the piping portion connecting the reaction tube 110A and the reaction tube 110B. That is, in the catalyst layer having length of 120 cm and consisting of catalyst layers 120A to 120C, the hydrogen gas (B) was dividedly introduced at two portions i.e. the catalyst layer 120A (0 cm point) and the catalyst layer 120B (40 cm point).

Further, the maximum temperature of the catalyst layers 120A to 120C during the reaction was measured by insertion-type thermometers 140A to 140C inserted respectively to such catalyst layers and found to be at most 130° C.

The obtained formed gas (D) was analyzed by GC, whereby the conversion ratio X was 65%.

Example 3

The reaction was carried out in the same manner as in Example 2 except that the carrier used for the catalyst was changed from silica gel to alumina (−5.6>H$_0$>−12).

The obtained formed gas (D) was analyzed by GC, whereby the conversion ratio X was 50%.

As shown in the foregoing, in Example 2 wherein a metal oxide having an acidity functional value (H$_0$) of at least −5.6 was used as a carrier, the conversion ratio X was high as compared with Example 3 wherein a metal oxide having an acidity function value (H$_0$) of less than −5.6 was used as a carrier.

INDUSTRIAL APPLICABILITY

The process of the present invention is very useful as a process for producing HFO-1234yf which is useful for e.g. a refrigerant, since the durability of the catalyst is high, and the conversion ratio to the desired product is also high.

The entire disclosures of Japanese Patent Application No. 2010-142668 filed on Jun. 23, 2010 and U.S. Provisional Patent Application No. 61/365,575 filed on Jul. 19, 2010 including specifications, claims, drawings and summaries are incorporated herein by reference in their entireties.

What is claimed is:

1. A process for producing 2,3,3,3-tetrafluoropropene, which comprises reacting a raw material compound of at least one of 1,1-dichloro-2,3,3,3-tetrafluoropropene and 1-chloro-2,3,3,3-tetrafluoropropene, and hydrogen, in the presence of a catalyst, wherein the catalyst is a noble metal catalyst supported on a metal oxide having a Hammett acidity function value (H$_0$) of at least −5.6.

2. The process for producing 2,3,3,3-tetrafluoropropene according to claim 1, wherein the noble metal is palladium.

3. The process for producing 2,3,3,3-tetrafluoropropene according to claim 1 or 2, wherein the metal oxide is silicon dioxide, titanium dioxide or zirconium dioxide.

4. The process for producing 2,3,3,3-tetrafluoropropene according to claim 1 or 2, wherein the metal oxide is silicon dioxide.

5. The process for producing 2,3,3,3-tetrafluoropropene according to claim 1 or 2, wherein the noble metal catalyst-supporting metal oxide has a specific surface area of from 10 to 1,000 m$^2$/g.

6. The process for producing 2,3,3,3-tetrafluoropropene according to claim 1 or 2, wherein to a catalyst layer packed with the catalyst-supporting metal oxide, the raw material compound and the hydrogen are introduced and reacted in a gas phase.

7. The process for producing 2,3,3,3-tetrafluoropropene according to claim 6, wherein the raw material compound and the hydrogen are introduced to a gas inlet portion of the catalyst layer, and hydrogen is introduced from at least one position between the gas inlet portion and a gas outlet portion of the catalyst layer.

8. The process for producing 2,3,3,3-tetrafluoropropene according to claim 6, wherein the ratio of the hydrogen to the raw material compound to be introduced to the catalyst layer is at most 0.7 as represented by the ratio of the number of moles of the hydrogen to the number of moles of chlorine atoms in the raw material compound ($H_2/Cl$).

9. The process for producing 2,3,3,3-tetrafluoropropene according to claim 6, wherein the linear velocity u of the raw material compound gas represented by the following formula (I) in the catalyst layer is from 1 to 30 cm/sec:

$$u=(W/100) \times V/S \quad (I)$$

(in the formula (I), W is the concentration (mol %) of the raw material compound gas in the entire gas flowing through the catalyst layer, V is the flow rate ($cm^3$/sec) of the entire gas flowing through the catalyst layer, and S is the cross-sectional area ($cm^2$) of the catalyst layer to the flow direction of the gas).

10. The process for producing 2,3,3,3-tetrafluoropropene according to claim 1 or 2, wherein the raw material compound is 1,1-dichloro-2,3,3,3tetrafluoropropene, or a mixture of 1,1-dichloro-2,3,3,3-tetrafluoropropene and 1-chloro-2,3,3,3-tetrafluoropropene, wherein based on the total number of moles of the two, the proportion of 1,1-dichloro-2,3,3,3-tetrafluoropropene is at least 50 mol %.

11. The process for producing 2,3,3,3-tetrafluoropropene according to claim 1, wherein the noble metal is palladium or a palladium alloy.

12. The process for producing 2,3,3,3-tetrafluoropropene according to claim 1, wherein the noble metal comprises palladium, rhodium, platinum, iridium, ruthenium, osmium or gold.

13. The process for producing 2,3,3,3-tetrafluoropropene according to claim 1, wherein a metal other than a noble metal is supported on the metal oxide.

14. The process for producing 2,3,3,3-tetrafluoropropene according to claim 13, wherein the metal other than a noble metal is at least one of iron, cobalt and nickel.

15. The process for producing 2,3,3,3-tetrafluoropropene according to claim 13, wherein the catalyst is in the form of a layer and the maximum temperature of the layer is 130° C.

16. The process for producing 2,3,3,3-tetrafluoropropene according to claim 6, wherein the ratio of the hydrogen to the raw material compound to be introduced to the catalyst layer is at most 0.6 as represented by the ratio of the number of moles of the hydrogen to the number of moles of chlorine atoms in the raw material compound ($H_2/Cl$).

17. The process for producing 2,3,3,3-tetrafluoropropene according to claim 6, wherein the ratio of the hydrogen to the raw material compound to be introduced to the catalyst layer is at most 0.5 as represented by the ratio of the number of moles of the hydrogen to the number of moles of chlorine atoms in the raw material compound ($H_2/Cl$).

18. The process for producing 2,3,3,3-tetrafluoropropene according to claim 1, wherein the noble metal is palladium or a palladium alloy and wherein the metal oxide is silicon dioxide.

* * * * *